United States Patent
Bernhardt et al.

(10) Patent No.: US 9,504,435 B2
(45) Date of Patent: Nov. 29, 2016

(54) METHOD AND DEVICE FOR AUTOMATED DETECTION OF THE CENTRAL LINE OF AT LEAST ONE PORTION OF A TUBULAR TISSUE STRUCTURE

(75) Inventors: Dominik Bernhardt, Hausen (DE); Christina Biermann, Hausen (DE); Michael Scheuering, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 709 days.

(21) Appl. No.: 12/828,364

(22) Filed: Jul. 1, 2010

(65) Prior Publication Data

US 2011/0158495 A1   Jun. 30, 2011

(30) Foreign Application Priority Data

Jul. 8, 2009 (DE) .................. 10 2009 032 257

(51) Int. Cl.
*G06K 9/00* (2006.01)
*A61B 5/05* (2006.01)
(Continued)

(52) U.S. Cl.
CPC ............. *A61B 6/504* (2013.01); *G06T 7/0085* (2013.01); *G06T 19/00* (2013.01); *A61B 5/055* (2013.01);
(Continued)

(58) Field of Classification Search
CPC ............ G06T 2207/20164; G06T 2207/10072; G06T 2207/10132; G06T 2207/30172;
(Continued)

(56) References Cited

U.S. PATENT DOCUMENTS 6,643,533 B2 * 11/2003 Knoplioch et al. ............ 600/407
6,978,549 B2 * 12/2005 Ellis .............................. 33/17 R
(Continued)

FOREIGN PATENT DOCUMENTS

WO   WO 2008138140 A1   11/2008

OTHER PUBLICATIONS

Tsai, C.L. et al., "Model-Based Method for Improving the Accuracy and Repeatability of Estimating Vascular Bifurcations and Crossovers From Retinal Fundus Images", In: IEEE Transactions on Information Technology in Biomedicine, vol. 8, No. 2, Jun. 2004; Others; 2004.
(Continued)

*Primary Examiner* — Hiep V Nguyen
(74) *Attorney, Agent, or Firm* — Harness, Dickey & Pierce, P.L.C.

(57) ABSTRACT

A method and a device are disclosed for automated detection of at least one part of the central line of at least one portion of a tubular tissue structure. In at least one embodiment of the method, characteristic landmarks of the tubular tissue structure are detected in a 3D data record of the tubular tissue structure; the detected characteristic landmarks of the tubular tissue structure and landmarks of a model of landmarks, which model belongs to the tubular tissue structure and takes into account the position of the landmarks relative to one another, are related to one another such that at least one portion of the tubular tissue structure is identified in the 3D data record of the tubular tissue structure. The central line of the identified portion of the tubular tissue structure is determined at least in part on the basis of at least one detected characteristic landmark and/or at least one landmark of the model of landmarks.

17 Claims, 2 Drawing Sheets

(51) Int. Cl.
  *A61B 6/00* (2006.01)
  *G06T 7/00* (2006.01)
  *G06T 19/00* (2011.01)
  *A61B 5/055* (2006.01)

(52) U.S. Cl.
  CPC ...... *A61B 6/506* (2013.01); *G06T 2207/10072* (2013.01); *G06T 2207/10132* (2013.01); *G06T 2207/20164* (2013.01); *G06T 2207/30172* (2013.01)

(58) Field of Classification Search
  CPC .................. G06T 7/0012; A61B 5/055; A61B 6/506
  USPC ........................................................ 382/131
  See application file for complete search history.

(56) References Cited

U.S. PATENT DOCUMENTS

| | | |
|---|---|---|
| 2007/0147707 A1 | 6/2007 | Coste-Maniere et al. |
| 2008/0085042 A1 | 4/2008 | Trofimov et al. |
| 2008/0132774 A1 | 6/2008 | Milstein et al. |
| 2010/0309198 A1* | 12/2010 | Kauffmann .................. 345/419 |

OTHER PUBLICATIONS

S.Kevin Zhou et al., "A probabilistic, hierarchical, and discriminant framework for rapid and accurate detection of deformable anatomic structure", Computer Vision, 2007, ICCV 2007, IEEE 11th Int. Conf. on Oct. 14-21, 2007, Rio de Janeiro, Brazil, pp. 1-8; Others; 2007.

* cited by examiner

FIG 1

METHOD AND DEVICE FOR AUTOMATED DETECTION OF THE CENTRAL LINE OF AT LEAST ONE PORTION OF A TUBULAR TISSUE STRUCTURE

PRIORITY STATEMENT

The present application hereby claims priority under 35 U.S.C. §119 on German patent application number DE 10 2009 032 257.4 filed Jul. 8, 2009, the entire contents of which are hereby incorporated herein by reference.

FIELD

At least one embodiment of the invention generally relates to a method and/or a device for automated detection of at least one part of the central line of at least one portion of a tubular tissue structure imaged or contained in a 3D data record.

BACKGROUND

In medical technology, obtaining image information from the interior of the body of patients using imaging scanners is routine and this information often forms the basis of a diagnosis. Thus, for example, a 3D data record of a vessel system is generated in CT angiography after the administration of a contrast agent and this 3D data record allows a medical practitioner to diagnose deformations of vessels, such as stenoses or aneurysms. For this, the medical practitioner is generally provided with a so-called CPR (curved multiplanar reconstruction) for an overview of a vessel of the vessel system, which CPR is based on determining the central line in the image of the vessel. Using the CPR, the medical practitioner can obtain a first overview of the state of the observed vessel and, for example, can determine the positions for measuring the vessel.

Here, measuring a vessel on the basis of the CPR takes up significantly less time than generating the central lines in the vessel system in the 3D data record. For this, the medical practitioner must in each case place one or more points of a vessel in the image so that the central line is automatically generated by software in the image of the respective vessel. In the case of much branched vessel systems, this requires a considerable amount of time.

SUMMARY

In at least one embodiment, a method and a device are specified such that determining a central line in a vessel of a vessel system or in a tubular tissue structure is simplified.

According to at least one embodiment of the invention, a method is disclosed for automated detection of at least one part of the central line of at least one portion of a tubular tissue structure, in which characteristic, preferably anatomical, landmarks of the tubular tissue structure are first of all detected in a 3D data record of the tubular tissue structure. The detection of the characteristic landmarks in the 3D data record can for example be brought about on the basis of the method described by S. Zhou et al. in "A probabilistic, hierarchical, and discriminant framework for rapid and accurate detection of deformable anatomic structure", Computer Vision, 2007, ICCV 2007, IEEE 11th International Conference on 14-21 Oct. 2007, Rio de Janeiro, Brazil, pages 1-8, the entire contents of which are hereby incorporated herein by reference.

The detected characteristic landmarks of the tubular tissue structure and landmarks of a model of landmarks, which model fits with or belongs to the tubular tissue structure and takes into account the position of the landmarks relative to one another, are related to one another such that at least one portion of the tubular tissue structure is identified in the 3D data record of the tubular tissue structure. Here, the model is not a general model of the tubular tissue structure to be examined per se, but it is only a general model of certain anatomical landmarks of the observed tubular tissue structure in the form of a knowledge base, in particular comprising the knowledge relating to the usual spatial position or arrangement of certain anatomical landmarks of the tubular tissue structure relative to one another, and hence also comprising the knowledge relating to the portions belonging to the tubular tissue structure.

By way of example, if the tubular tissue structure is the vessel structure or part of the vessel structure of the arteries in a human, the model of landmarks of the vessel structure of the arteries for example comprises as certain anatomical landmarks: the aorta—brachiocephalic artery bifurcation, the aorta—(left) common carotid artery bifurcation, the aorta—(left) subclavian artery bifurcation, the (left and right) internal/external carotid artery bifurcation, the position in the aorta level with the renal artery, the (left and right) common iliac artery bifurcation etc. and their usual spatial position relative to one another.

If the characteristic landmarks detected in the 3D data record and the certain landmarks of the model of landmarks are put in relation to one another, for example by similarity analysis of their spatial position or their spatial distribution relative to one another, it is possible to identify not only the detected characteristic landmarks but also the corresponding portions of the tubular tissue structure in the 3D data record.

The central line of the identified portion of the tubular tissue structure is determined at least in part on the basis of at least one detected characteristic landmark and/or at least one landmark of the model of landmarks, provided no second detected characteristic landmark is available for an identified portion of the tubular tissue structure, and so a CPR of the portion can for example be generated. The central line can be determined on the basis of the landmarks by way of an algorithm from graph-theory, for example by means of the A* algorithm or Dijkstra's algorithm.

According to at least one embodiment of the invention, the central lines of the portions of a tubular tissue structure in a 3D data record can thus be determined in a fully automatic fashion and without user interaction in a simplified fashion. Hence, the time-consuming placement of points in portions of the tubular tissue structure is no longer required for determining the central line, which determination is carried out for preparing the generation of one or more CPRs.

The model of landmarks generally has more landmarks than are contained or detected in the 3D data record. According to one variant of at least one embodiment of the invention, the model of landmarks has at least one further landmark assigned to at least one portion of the tubular tissue structure, which portion is only partly contained in the 3D data record, wherein the at least one further landmark of the model of landmarks cannot be put into relation with the corresponding characteristic landmark of the tubular tissue structure because the corresponding characteristic landmark of the portion is not imaged in the 3D data record. This variant of at least one embodiment of the invention is based on the consideration that portions of the tubular tissue structure are generally only contained in part or in an incomplete fashion, particularly at the edges, in the 3D data record of the tubular tissue structure.

Accordingly, the central line of such a portion only partly contained could not be determined where a second characteristic landmark, assigned to the end of the portion not contained in the 3D data record, is lacking. However, should the landmark be provided by the model of landmarks, a further variant of at least one embodiment of the invention allows the portion of the tubular tissue structure only partly contained in the 3D data record to be identified on the basis of the at least one further landmark of the model of landmarks and the central line of the identified portion of the tubular tissue structure to be at least partly determined.

One embodiment of the invention provides for the at least one identified portion of the tubular tissue structure to be provided with its anatomical designation. In general, all portions of the tubular tissue structure identified in the 3D data record are provided with their corresponding anatomical designation, which simplifies subsequent work, e.g. diagnosing using the 3D data record.

According to a further embodiment of the invention, a CPR (curved multiplanar reconstruction) is generated from the at least one identified portion of the tubular tissue structure, the central line of which has been determined, which CPR can be provided, for example, to a medical practitioner for diagnosing the portion.

According to one variant of at least one embodiment of the invention, the 3D data record is generated using an X-ray computed tomography scanner, a C-arc X-ray scanner, a magnetic resonance scanner or an ultrasound scanner.

At least one embodiment of the invention is also achieved by a device with a storage unit comprising the model of landmarks and with calculation segments for carrying out one of the methods described above.

More particularly, for obtaining the 3D data record, the device preferably has, as mentioned previously, an X-ray computed tomography scanner, a C-arc X-ray scanner, a magnetic resonance scanner or an ultrasound scanner.

BRIEF DESCRIPTION OF THE DRAWINGS

An example embodiment of the invention is illustrated in the attached schematic drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
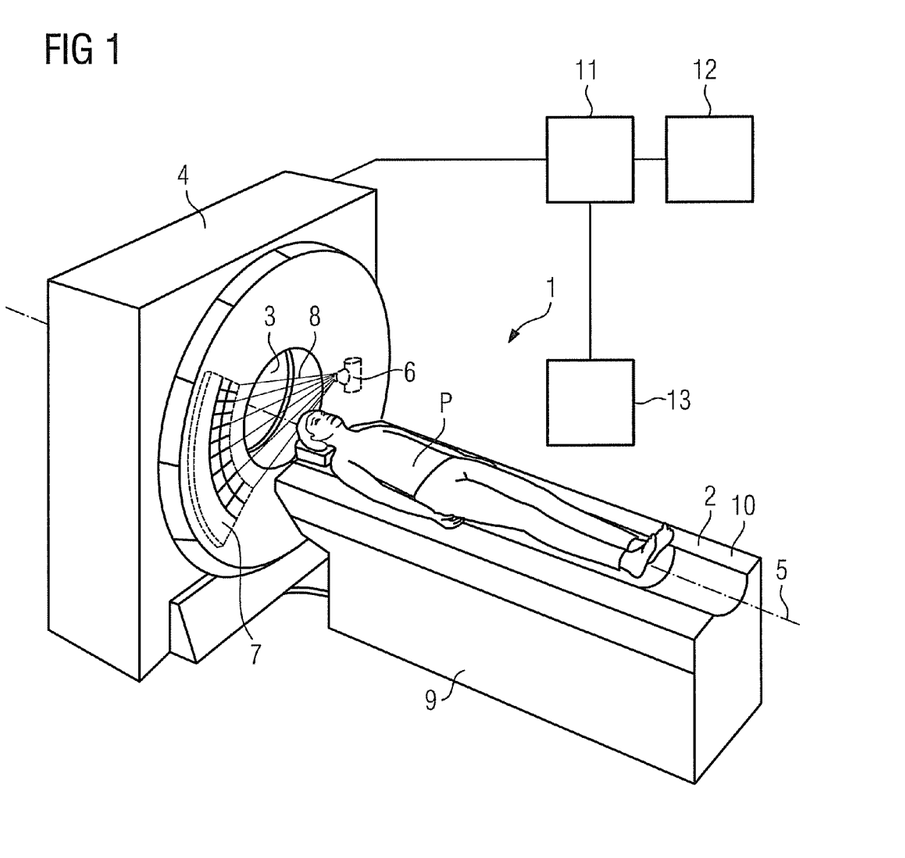
FIG. 1 shows a device with a computed tomography scanner for carrying out the method for automated detection of the central lines of a tubular tissue structure and FIG. 2 shows a 3D data record with anatomical landmarks of the vessel structure of arteries of a human.

In the figures, equivalent or functionally equivalent elements are always provided with the same reference signs. The illustrations in the figures are schematic and not necessarily true to scale. In the following text, and without loss of generality, the X-ray computed tomography scanner 1 illustrated in FIG. 1 is only addressed to the extent considered necessary for understanding embodiments of the invention.

The X-ray computed tomography scanner 1 shown in figure has a patient couch 2 for supporting a patient P to be examined. The X-ray computed tomography scanner 1 furthermore comprises a gantry 4 with a tube-detector system mounted such that it can rotate about a system axis 5. The tube-detector system has an X-ray tube 6 and an X-ray detector unit 7 that mutually oppose one another. During operation, X-ray radiation 8 is emitted from the X-ray tube 6 in the direction of the X-ray detector unit 7 and registered by the latter.

The patient couch 2 has a couch base 9, on which there is arranged a patient support table 10 provided to actually support the patient P. The patient support table 10 can be adjusted relative to the couch base 9 such that the patient support table 10 with the patient P can be inserted into the opening 3 of the gantry 4 for the purpose of recording 2D X-ray projections of the patient P, for example in a spiral scan. The computational processing of the 2D X-ray projections, or the reconstruction of slice images, 3D images or a 3D data record on the basis of the 2D X-ray projections is performed by an image computer (not explicitly illustrated) of the X-ray computed tomography scanner 1, which slice images or 3D images can be displayed on a display device.

In the present example embodiment of the invention, part of the vessel structure of the arteries in the patient P is intended to be examined. For this, a 3D data record, as illustrated schematically in FIG. 2, of the vessel structure of the arteries to be examined is first of all reconstructed using the X-ray computed tomography scanner 1, generally after the administration of a contrast agent.

Figure 2:
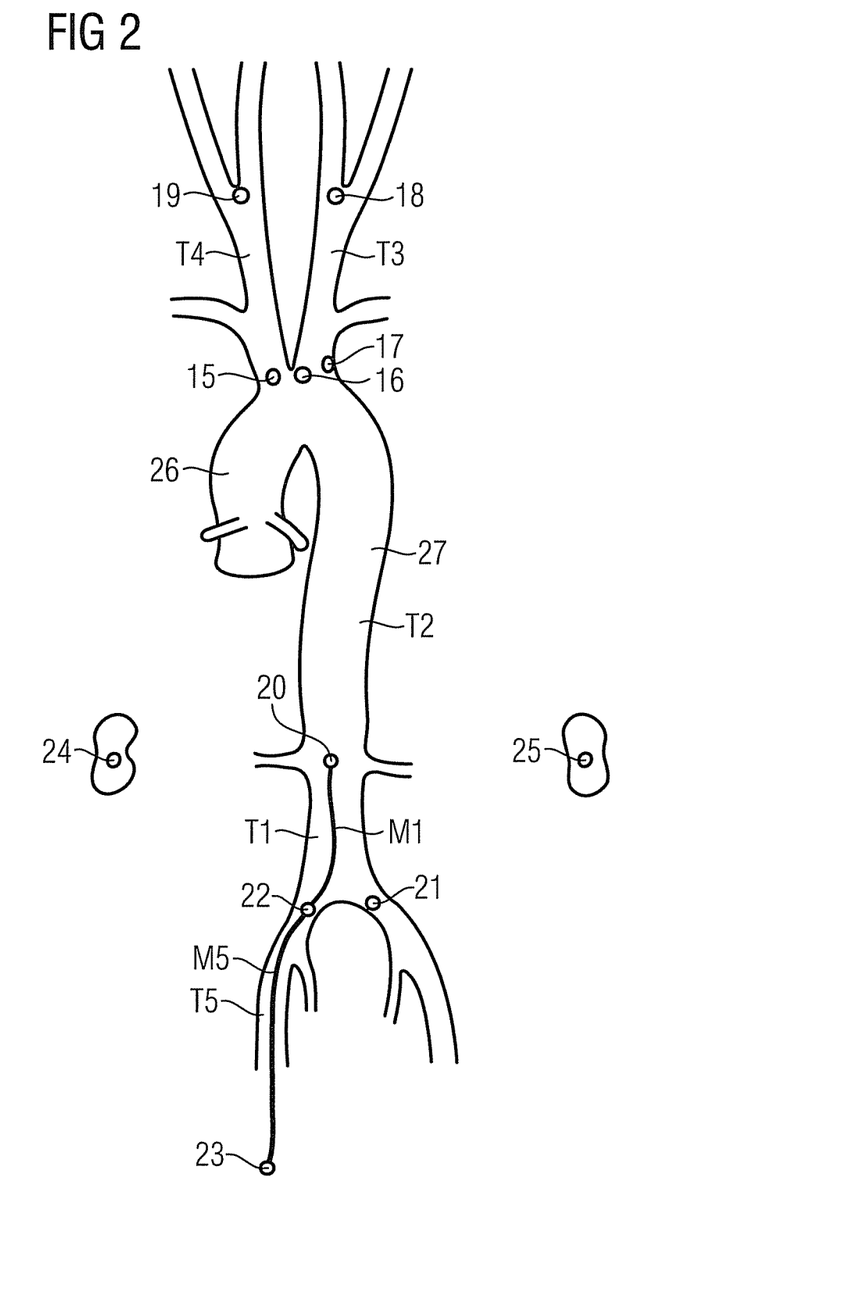

In order to diagnose the vessel structure of the arteries, it is desirable to provide the diagnosing medical practitioner with a CPR (curved multiplanar reconstruction) in a usual fashion, on the basis of which CPR the medical practitioner can obtain an overview of the state of the vessel structure of the arteries. For this, it is necessary to determine in the 3D data record the central lines of the imaged arteries. In order to be able to bring this about quickly and efficiently, a general model of anatomical landmarks fitting with or belonging to the vessel structure of the arteries is kept ready in a storage unit 12 in the case of the present example embodiment of the invention, which model comprises knowledge relating to the usual spatial location or arrangement of certain anatomical landmarks of the vessel structure of the arteries relative to one another, and knowledge relating to the portions belonging to the vessel structure of the arteries. Here, the model is designed with respect to the build or physique of an average person, but can be fitted dynamically within certain limits to, for example, the size of the current patient P to be examined by means of scaling factors.

In the case of the present example embodiment of the invention, the model of anatomical landmarks of the vessel structure of the arteries inter alia stores the following certain anatomical landmarks and their usual spatial arrangement with respect to one another:

the aorta—brachiocephalic artery bifurcation,
the aorta—(left) common carotid artery bifurcation,
the aorta—(left) subclavian artery bifurcation,
the (left) internal/external carotid artery bifurcation,
the (right) internal/external carotid artery bifurcation,
the position in the aorta level with the renal artery,
the (left) common iliac artery bifurcation,
the (right) common iliac artery bifurcation.

The aforementioned certain anatomical landmarks of the model of landmarks only constitute a selection for explaining embodiments of the invention. The model of anatomical landmarks of the vessel structure of the arteries stored in the storage unit 12 can still thus have a multiplicity of further certain anatomical landmarks, for example a landmark assigned to the right popliteal artery, which right popliteal artery is not contained in the 3D data record in FIG. 2. Likewise, the model of anatomical landmarks of the vessel structure of the arteries can also have further landmarks assigned to, for example, organs, e.g. the kidneys, or other tissue types.

Once the 3D data record of the vessel structure of the arteries in the patient P has been reconstructed, as illustrated in FIG. 2, and provided to a computer 11 by the X-ray computed tomography scanner 1, the computer 11 is first of all used to detect the characteristic landmarks, in the case of the present example embodiment of the invention the characteristic anatomical landmarks, of the vessel structure of the arteries in the 3D data record.

In the case of the present example embodiment of the invention, the characteristic anatomical landmarks of the vessel structure of the arteries are mainly the bifurcations or ramifications of the arteries, starting from the ascending aorta 26 and the descending aorta 27. For this, the computer 11 has been provided with appropriate software, which can for example be based on the method described by S. Zhou et al. in "A probabilistic, hierarchical, and discriminant framework for rapid and accurate detection of deformable anatomic structure", Computer Vision, 2007, ICCV 2007, IEEE 11th International Conference on 14-21 Oct. 2007, Rio de Janeiro, Brazil, pages 1-8, the entire contents of which are hereby incorporated herein by reference.

Alternatively, the anatomical landmarks or ramifications of the arteries can also be detected manually by user inputs, as a result of which the method per se is not significantly slowed down.

While the anatomical landmarks are detected in the 3D data record, whether this is the automated or the manual detection, it is only the ramifications per se which are detected or denoted as characteristic landmarks, without the respective ramifications being identified in a precise fashion. Then, all ramifications in the 3D data record are preferably, but not necessarily, denoted as characteristic landmarks as a result of this method step.

The detected characteristic anatomical landmarks in the 3D data record and the anatomical landmarks of the model of anatomical landmarks belonging to the vessel structure of the arteries are subsequently put into relation with one another. This can be brought about by the model of anatomical landmarks being registered in an affine fashion to the detected characteristic anatomical landmarks, the registration being brought about in the sense of approximate imaging, which can be performed by similarity analysis.

If the characteristic anatomical landmarks detected in the 3D data record and the anatomical landmarks of the model of landmarks have been put into relation with one another, or imaged on one another, it is possible for the individual ramifications of the arteries and the arteries to be identified in the 3D data record due to knowledge from the model relating to the spatial arrangement of the anatomical landmarks or the ramifications of the arteries relative to one another and due to the knowledge from the model relating to the associated ramifications and arteries per se.

Thus, for example, the knowledge from the model allows the identification of the position 15 as the aorta brachiocephalic artery bifurcation, the position 16 as the aorta—(left) common carotid artery bifurcation, the position 17 as the aorta—(left) subclavian artery bifurcation, the position 18 as the (left) internal/external carotid artery bifurcation, the position 19 as the (right) internal/external carotid artery bifurcation, the position 20 as the position in the aorta level with the renal artery, the position 21 as the (left) common iliac artery bifurcation, and the position 22 as the (right) common iliac artery bifurcation, and the plotting thereof in the 3D data record with their correct anatomical designation. The correct anatomical designations of the arteries can likewise be plotted in the 3D data record. As a further output of the model of anatomical landmarks, landmarks belonging to arteries not imaged in the 3D data record can be plotted in the 3D data record. In the present case, the landmark 23 is plotted in the 3D data record in an example fashion, which landmark is assigned to the right popliteal artery.

The anatomical landmarks identified in the 3D data record or in the images of the arteries in the 3D data record represent the starting points for the automated determination of the central lines in the respective arteries. Landmarks 20 and 22 are selected for this in an example fashion. For example, by applying the A* algorithm or Dijkstra's algorithm, the central line M1 in the portion T1 of the descending aorta between the landmarks 20 and 22 can be determined by the computer 11 and plotted in the 3D data record. Subsequently, a CPR can be generated for this portion T1 of the descending aorta and can be displayed on a visualization instrument 13 in order to be able to undertake a diagnosis of the portion T1.

The central lines of the arteries can also be determined in a corresponding fashion in portions T2 to T4 and plotted in the 3D data record.

There is no further characteristic anatomical landmark available in the 3D data record in addition to the characteristic landmark 22 for determining the central line of the portion T5 if the portion T5 of the right external iliac artery is also intended to be diagnosed. For this, use is made in the present case of the landmark 23 that originates from the model of anatomical landmarks and is assigned to the popliteal artery, itself not imaged in the 3D data record, and so the central line M5 can be determined and a CPR of the portion T5 can be generated and displayed.

This allows the determination of the central lines of the arteries in an automated fashion for the entire tissue structure of the arteries imaged in the 3D data record and the generation and the provision of CPRs for the diagnosis.

Characteristic landmarks of portions of the tubular tissue structure missing from or not identified in the 3D data record can be replaced by landmarks from the model of landmarks in the process, and so the central lines can also be determined for the affected portions of the tubular tissue structure. Since the process of determining the central lines is preferably carried out automatically, diagnosing the tubular tissue structure is possible to all intents and purposes without waiting for a medical practitioner undertaking the diagnosis.

The results of the method according to an embodiment of the invention, or the anatomical knowledge obtained with the aid of the method according to an embodiment of the invention, can also be used during interactive work with the 3D data record, more particularly also during the determination of a vessel central line by manual definition of two points, for the best possible parameterization of the algorithms, depending on the respective body region and the anatomical neighborhood, and to thereby obtain more robust results.

In the case of the present example embodiment of the invention, the 3D data record was generated using an X-ray computed tomography scanner. However, the 3D data record can also be generated using a magnetic resonance scanner, a C-arc X-ray scanner or an ultrasound scanner. Which imaging scanner is used for generating the 3D data record depends inter alia on the tubular tissue structure to be examined.

The application of embodiments of the method are not restricted to the tissue structure of arteries. Rather, the embodiments of the method can also be applied to other tubular tissue structures, for example to different types of blood vessels or to nerve tracts, etc.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automated detection of at least one part of a central line of at least one portion of a tubular tissue structure of a current patient under examination, the method comprising:
    detecting, by a computer processor, characteristic landmarks of the tubular tissue structure in a 3D data record of the tubular tissue structure;
    identifying, by the computer processor, a set of anatomical landmarks of the at least one portion of the tubular tissue structure in the 3D data record based on a registration of the detected characteristic landmarks of the tubular tissue structure and landmarks of a model of landmarks, the identifying including,
        performing an affine transformation to register the characteristic landmarks and the model of the landmarks, and
        anatomically identifying each of the characteristic landmarks with a corresponding one of the landmarks of the model of landmarks such that each of the characteristic landmarks has a corresponding anatomical identification associated therewith, wherein the model of landmarks,
            is designed with respect to a build or physique of an average person,
            is scalable to fit a size of the current patient so that the landmarks of the model of landmarks indicate a usual spatial position or arrangement of parts of the tubular tissue structure, and
            is in the form of a knowledge base stored in a storage device;
    determining, by the computer processor, the central line of the at least one portion of the tubular tissue structure, at least in part, on a basis of a path-finding operation that uses the identified set of anatomical landmarks; and
    displaying, on a visualization instrument, a curved multiplanar reconstruction (CPR) of the at least one portion of the tubular tissue structure generated by the computer processor based on the central line thereof.

2. The method as claimed in claim 1, wherein the model of landmarks includes at least one further landmark assigned to at least one further portion of the tubular tissue structure, the at least one further portion being only partly contained in the 3D data record, wherein the at least one further landmark of the model of landmarks cannot be put into relation with a corresponding characteristic landmark of the tubular tissue structure because the corresponding characteristic landmarks of the at least one further portion are not imaged in the 3D data record.

3. The method as claimed in claim 2, wherein the at least one further portion of the tubular tissue structure only partly contained in the 3D data record is identified on a basis of the at least one further landmark of the model of landmarks, and the central line of the at least one portion of the tubular tissue structure is at least partly determined based on the identified at least one further portion.

4. The method as claimed in claim 1, wherein the at least one portion of the tubular tissue structure is provided with its anatomical designation.

5. The method as claimed in claim 1, wherein a CPR (curved multiplanar reconstruction) is generated from the at least one portion of the tubular tissue structure.

6. The method as claimed in claim 1, wherein the 3D data record is generated using an X-ray computed tomography scanner, a C-arc X-ray scanner, a magnetic resonance scanner or an ultrasound scanner.

7. The method of claim 1, wherein the model of landmarks has a greater number of landmarks than the detected characteristic landmarks.

8. The method of claim 1, wherein
    the identifying further includes registering the detected characteristic landmarks of the at least one portion of the tubular tissue structure from within the 3D date record with associated ones of the landmarks of the model of landmarks, and registering non-detected characteristic landmarks of at least one further portion of the tubular tissue structure not imaged in the 3D data record with associated ones of the landmarks of the model of landmarks by replacing the non-detected characteristic landmarks with the associated ones of the landmarks of the model, the determining determines the central line of the at least one further portion of the tubular tissue structure associated with the non-detected characteristic landmarks, and the displaying displays the curved multiplanar reconstruction (CPR) of the at least one portion and the at least one further portion of the tubular tissue structure generated by the computer processor based on the central line thereof.

9. A device for automated detection of at least one part of a central line of at least one portion of a tubular tissue structure of a current patient under examination, comprising:
a storage unit including a model of landmarks; and
at least one calculation device configured to,
  detect characteristic landmarks of the tubular tissue structure in a 3D data record of the tubular tissue structure,
  identify a set of anatomical landmarks of at least one portion of the tubular tissue structure in the 3D data record based on a registration of the detected characteristic landmarks of the tubular tissue structure and landmarks of the model of landmarks, wherein the model of landmarks, the least one calculation device configured to identify the set of anatomical landmarks by,
  performing an affine transformation to register the characteristic landmarks and the model of the landmarks, and
  anatomically identifying each of the characteristic landmarks with a corresponding one of the landmarks of the model of landmarks such that each of the characteristic landmarks has a corresponding anatomical identification associated therewith,
    is designed with respect to a build or physique of an average person,
    is scalable to fit a size of the current patient so that the landmarks of the model of landmarks indicate a usual spatial position or arrangement of parts of the tubular tissue structure, and
    is in the form of a knowledge base stored in a storage device,
  determine the central line of the portion of the tubular tissue structure, at least in part, on a basis of a path-finding operation that uses the identified set of anatomical landmarks; and
  display, on a visualization instrument, a curved multiplanar reconstruction (CPR) of the at least one portion of the tubular tissue structure generated by the at least one calculation device based on the central line thereof.

10. The device as claimed in claim 9, further comprising:
an X-ray computed tomography scanner, a C-arc X-ray scanner, a magnetic resonance scanner or an ultrasound scanner.

11. The device of claim 9, wherein the model of landmarks has a greater number of landmarks than the detected characteristic landmarks.

12. The device of claim 9, wherein, the at least one calculation device is configured to,
identify the set of anatomical landmarks by registering the detected characteristic landmarks of the at least one portion of the tubular tissue structure from within the 3D date record with associated ones of the landmarks of the model of landmarks, and registering non-detected characteristic landmarks of at least one further portion of the tubular tissue structure not imaged in the 3D data record with associated ones of the landmarks of the model of landmarks by replacing the non-detected characteristic landmarks with the associated ones of the landmarks of the model, determine the central line of the at least one further portion of the tubular tissue structure associated with the non-detected characteristic landmarks, and display, on the visualization instrument, the curved multiplanar reconstruction (CPR) of the at least one portion and the at least one further portion of the tubular tissue structure generated by the at least one calculation device based on the central line thereof.

13. A non-transitory computer readable medium including program segments for, when executed on a computer processor, causing the computer processor to carry out a method for automated detection of at least one part of a central line of at least one portion of a tubular tissue structure of a current patient under examination, the method comprising:
detecting characteristic landmarks of the tubular tissue structure in a 3D data record of the tubular tissue structure;
identifying, by the computer processor, a set of anatomical landmarks of the at least one portion of the tubular tissue structure in the 3D data record based on a registration of the detected characteristic landmarks of the tubular tissue structure and landmarks of a model of landmarks, the identifying including,
  performing an affine transformation to register the characteristic landmarks and the model of the landmarks, and
  anatomically identifying each of the characteristic landmarks with a corresponding one of the landmarks of the model of landmarks such that each of the characteristic landmarks has a corresponding anatomical identification associated therewith, wherein the model of landmarks,
    is designed with respect to a build or physique of an average person,
    is scalable to fit a size of the current patient so that the landmarks of the model of landmarks indicate a usual spatial position or arrangement of parts of the tubular tissue structure, and
    is in the form of a knowledge base stored in a storage device;
determining the central line of the at least one portion of the tubular tissue structure, at least in part, on a basis of a path-finding operation that uses the identified set of anatomical landmarks; and
displaying, on a visualization instrument, a curved multiplanar reconstruction (CPR) of the at least one portion of the tubular tissue structure generated by the computer processor based on the central line thereof.

14. The method of claim 13, wherein the model of landmarks has a greater number of landmarks than the detected characteristic landmarks.

15. The non-transitory computer readable medium of claim 13, wherein
the identifying further includes registering the detected characteristic landmarks of the at least one portion of the tubular tissue structure from within the 3D date record with associated ones of the landmarks of the model of landmarks, and registering non-detected characteristic landmarks of at least one further portion of the tubular tissue structure not imaged in the 3D data record with associated ones of the landmarks of the model of landmarks by replacing the non-detected characteristic landmarks with the associated ones of the landmarks of the model, the determining determines the central line of the at least one further portion of the tubular tissue structure associated with the non-detected characteristic landmarks, and the displaying displays the curved multiplanar reconstruction (CPR) of the at least one portion and the at least one further portion of the tubular tissue structure generated by the computer processor based on the central line thereof.

16. A method for automated detection of at least one part of a central line of at least one portion of a tubular tissue structure, the method comprising:

detecting, by a processor, characteristic landmarks of the tubular tissue structure in a 3D data record of the tubular tissue structure;

identifying, by the processor, a set of anatomical landmarks of the at least one portion of the tubular tissue structure in the 3D data record of the tubular tissue structure based on the detected characteristic landmarks of the tubular tissue structure and landmarks of a model of landmarks, the identifying including, performing an affine transformation to register the characteristic landmarks and the model of the landmarks, and anatomically identifying each of the characteristic landmarks with a corresponding one of the landmarks of the model of landmarks such that each of the characteristic landmarks has a corresponding anatomical identification associated therewith, wherein the model of landmarks, is designed with respect to a build or physique of an average person, is scalable to fit a size of the current patient so that the landmarks of the model of landmarks indicate a usual spatial position or arrangement of parts of the tubular tissue structure, and is in the form of a knowledge base stored in a storage device, the knowledge base indicating the usual spatial position or arrangement of the desired anatomical landmarks with respect to one another; and determining, by the processor, the central line of the identified portion of the tubular tissue structure, at least in part, on a basis of a path-finding operation that uses the identified set of anatomical landmarks; and displaying, on a visualization instrument, a curved multiplanar reconstruction (CPR) of the at least one portion of the tubular tissue structure generated by the processor based on the central line thereof, the model of landmarks having a greater number of landmarks than the detected characteristic landmarks.

17. The method of claim 16, wherein the identifying further includes registering the detected characteristic landmarks of the at least one portion of the tubular tissue structure from within the 3D date record with associated ones of the landmarks of the model of landmarks, and registering non-detected characteristic landmarks of at least one further portion of the tubular tissue structure not imaged in the 3D data record with associated ones of the landmarks of the model of landmarks by replacing the non-detected characteristic landmarks with the associated ones of the landmarks of the model, the determining determines the central line of the at least one further portion of the tubular tissue structure associated with the non-detected characteristic landmarks, and the displaying displays the curved multiplanar reconstruction (CPR) of the at least one portion and the at least one further portion of the tubular tissue structure generated by the processor based on the central line thereof.

* * * * *